US00PP30320P2

(12) United States Plant Patent
Nishikawa

(10) Patent No.: US PP30,320 P2
(45) Date of Patent: Mar. 26, 2019

(54) ***DELOSPERMA* PLANT NAMED 'DE18-162'**

(50) Latin Name: *Delosperma cooperi*
Varietal Denomination: DE18-162

(71) Applicant: Koichiro Nishikawa, Katuta-Gun (JP)

(72) Inventor: Koichiro Nishikawa, Katuta-Gun (JP)

( * ) Notice: Subject to any disclaimer, the term of this patent is extended or adjusted under 35 U.S.C. 154(b) by 0 days.

(21) Appl. No.: 15/732,267

(22) Filed: Oct. 17, 2017

(51) Int. Cl.
*A01H 5/02* (2018.01)

(52) U.S. Cl.
USPC ..... Plt./422

(58) Field of Classification Search
USPC ..... Plt./263.1, 422
See application file for complete search history.

*Primary Examiner* — Susan McCormick Ewoldt
*Assistant Examiner* — Karen M Redden
(74) *Attorney, Agent, or Firm* — Penny J. Aguirre

(57) ABSTRACT

A new cultivar of *Delosperma* plant, 'DE18-162', characterized by its compact plant habit, its floriferous and long blooming flowering habit, its high heat tolerance, and its flowers that are true pink in color.

2 Drawing Sheets

Botanical classification: *Delosperma cooperi.*
Variety denomination: 'DE18-162'.

BACKGROUND OF THE INVENTION

The present invention relates to a new and distinct cultivar of *Delosperma* plant, botanically known as *Delosperma cooperi* 'DE18-162' and will be referred to hereinafter by its cultivar name, 'DE18-162'. The new cultivar of *Delosperma* is an herbaceous perennial grown for container and landscape use.

The new cultivar was derived from a controlled breeding program conducted by the Inventor in Ichinimiya-City, Aichi-Pref, Japan. The overall purpose of the breeding program was to develop new cultivars of *Delosperma* plants with low-growing and well-spreading growth habits combined with long flowering periods and a unique range of flower colors.

'DE18-162' arose from a crosses made by the Inventor between unnamed and unpatented proprietary plants of *Delosperma cooperi* from his breeding program. Seeds were pooled from the crosses and therefore the exact parentage is unknown. 'DE18-162' was selected in 2015 as a single unique plant amongst the resulting seedlings.

Asexual propagation of the new cultivar was first accomplished by softwood cuttings in 2015 by the Inventor in Ichinimiya-City, Aichi-Pref, Japan. Propagation by softwood cuttings has shown that the unique features of the new cultivar are stable and reproduced true to type in successive generations.

SUMMARY OF THE INVENTION

The following traits have been repeatedly observed and are determined to be the characteristics of the new cultivar. These attributes in combination distinguish 'DE18-162' as a unique cultivar of *Delosperma.*

1. 'DE18-162' exhibits a compact and horizontal plant habit
2. 'DE18-162' exhibits flowers that are true pink in color.

3. 'DE18-162' exhibits floriferous and long blooming flowering habit.
4. 'DE18-162' exhibits high heat tolerance.

'DE18-162' can be most closely compared to *Delosperma cooperi* cultivars 'Jewel of Desert Rosequartz' (U.S. Plant Pat. No. 23,452) and 'WOWDRY1' (U.S. Plant Pat. No. 26,157). 'Jewel of Desert Rosequartz' differs from 'DE18-162' in having flowers that are redder pink in color. 'WOWDRY1' differs from 'DE18-162' in having flowers with petals that are magenta pink towards the apex changing to red-pink and then yellow towards the base.

BRIEF DESCRIPTION OF THE DRAWINGS

The accompanying colored photographs illustrate the overall appearance and distinct characteristics of the new *Delosperma*. The plant in the photograph is 3 months in age as grown in a 1-liter container in an unheated greenhouse in Noordwijkerhout, The Netherlands.

The photograph in FIG. 1 provides a side view of 'DE18-162' in bloom.

Figure 1:
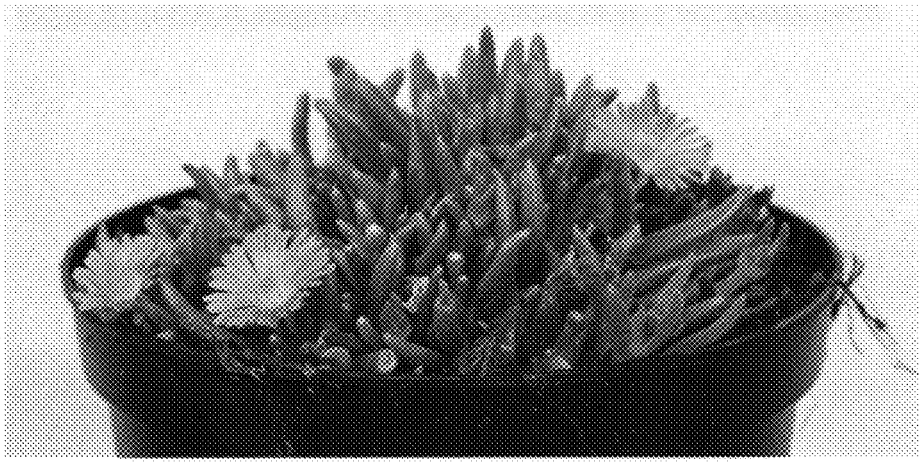
Figure 2:
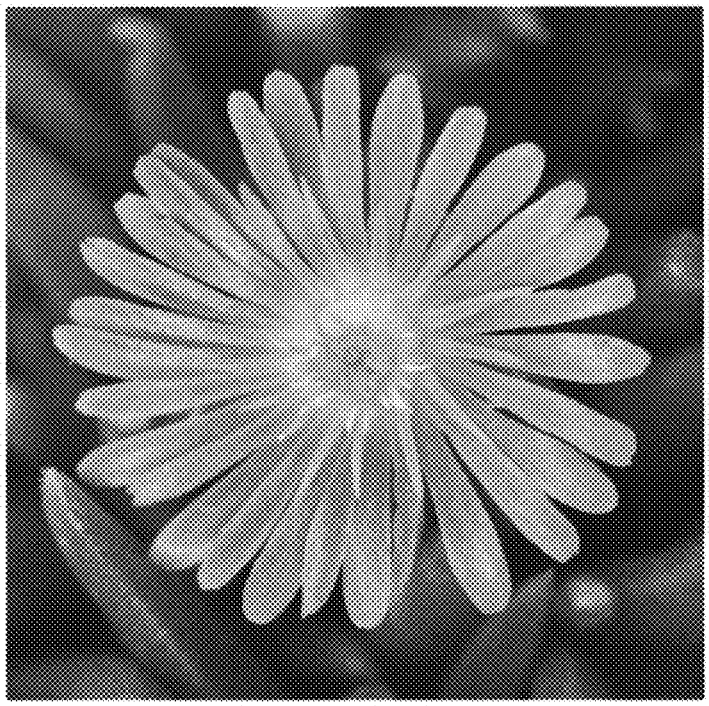

The photograph in FIG. 2 provides a close-up view of a flower of 'DE18-162'.

Figure 3:
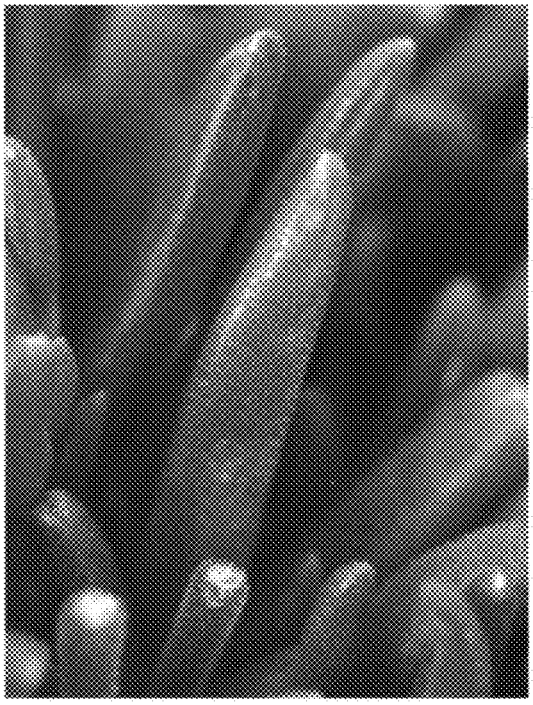

The photograph in FIG. 3 provides a close-up view of the foliage of 'DE18-162'.

The colors in the photographs may differ slightly from the color values cited in the detailed botanical description, which accurately describe the colors of the new *Delosperma.*

DETAILED BOTANICAL DESCRIPTION

The following is a detailed description of three month-old plants of the new cultivar as grown in a 1-liter container in an unheated greenhouse in Noordwijkerhout, The Netherlands. The phenotype of the new cultivar may vary with variations in environmental, climatic, and cultural conditions, as it has not been tested under all possible environmental conditions. The color determination is in accordance with The 2015 Royal Horticultural Society Colour Chart of The Royal Horticultural Society, London, England, except where general color terms of ordinary dictionary significance are used.

General description:

*Blooming period*.—Late spring to late summer in Boskoop, The Netherlands.

*Plant type*.—Herbaceous perennial.

*Plant habit*.—Compact, well-spreading, horizontal.

*Height and spread*.—Reaches about 5.1 cm in height and 13.8 cm in spread as grown in a 1-liter container.

*Cold hardiness*.—Observed to be hardy in U.S.D.A. Zones 7 to 12.

*Diseases and pests*.—No susceptibility to resistance to diseases or pests has been observed.

*Root description*.—Fibrous roots, 162D in color.

*Propagation*.—Softwood cuttings.

*Growth habit*.—Moderately vigorous.

*Root development*.—Roots initiate and fill a 104-cell plug in 3 weeks and the planted plugs fully develop in 9-cm container within 7 weeks.

Stem description:

*Shape*.—Round.

*Stem color*.—Young stems; 151D, mature stems; 163C.

*Stem size*.—Lateral branches; an average of 3.4 cm in length and 2 mm in diameter.

*Internode length*.—An average of 9 mm.

*Stem texture*.—Succulent.

*Stem surface*.—Moderately glossy.

*Stem aspect*.—Held in an average angle of 90°.

*Stem strength*.—Strong.

*Branching habit*.—An average of 15 primary branches, 30 lateral branches.

Foliage description:

*Leaf shape*.—Ligulate, triangular in diameter.

*Leaf substance*.—Succulent.

*Leaf division*.—Simple.

*Leaf base*.—Cuneate.

*Leaf apex*.—Acute.

*Leaf venation*.—No veins visible.

*Leaf margins*.—Entire.

*Leaf aspect*.—Slightly to moderately curved.

*Leaf arrangement*.—Opposite.

*Leaf surface*.—Both surfaces smooth, moderately glossy and densely covered with very short glandular hairs, average of 0.2 mm, very hard to measure color due to small size, closest to 157D in color.

*Leaf color*.—Upper surface; 143A, lower surface NN137B.

*Leaf size*.—About 3.7 cm in length and 4 mm in width.

*Leaf quantity*.—Average of 6 (3 pairs) per lateral branch.

*Leaf attachment*.—Sessile.

Inflorescence description:

*Inflorescence type*.—Flowers solitary.

*Flower number*.—An average of 3 flowers and 42 flower buds per plant.

*Flower fragrance*.—Faint, sweet and pleasant.

*Flower aspect*.—Upright to slightly outward.

*Flower longevity*.—Average of 6 days.

*Flower type*.—Single, rotate.

*Flower size*.—Average of 2.3 cm in height and diameter and 7 mm in depth.

*Flower buds*.—Ovate in shape, an average of 1.1 cm in length and 5 mm in diameter, 143A in color, base 144C in color, surface is slightly glossy and densely covered with very short glandular hairs; an average of 0.2 mm in length, 157D in color.

*Calyx*.—Rotate in shape, average of 6 mm in depth and 1.4 cm in diameter.

*Sepals*.—5, rotate, narrowly ovate in shape, an average of 5 mm in length and 2 mm in width, acute apex, broadly cuneate base, color; opening and fully open flowers upper and lower surface; 143B, margin entire, surfaces and margin moderately covered with very short glandular hairs an average of 0.2 mm in length and 157D in color.

*Petals*.—An average of 34 per flower, 2 whorls, rotate, narrowly oblanceolate in shape, upper and lower surface is glabrous, velvety and glossy, margin entire, apex obtuse, base narrowly cuneate, an average of 9 mm in length and 1.5 mm in width, color: opening and fully open flowers upper and lower surface; N74B, non fading.

*Petaloids*.—None present.

*Peduncle*.—None present.

*Pedicel*.—Average of 1.2 cm in length and 1.75 mm in diameter, held straight on top of lateral branch at 0° to 30°, 145A in color, surface slightly glossy, moderately strong in strength, 145A in color, surface is slightly glossy and densely covered with very short glandular hairs an average of 0.2 mm in length and 157D in color.

Reproductive organs:

*Pistils*.—Average of 5, style and stigma; no separate stigma and style visible (not distinguishable), triangular in shape, are an average of 2 mm in length, 0.75 mm in diameter and N144B in color, ovary; 144A in color.

*Stamens*.—Average 50, anthers; dorsifixed and ovate in shape, an average of 0.5 mm in length and 0.2 mm in width, 12A in color, filaments; 1.5 mm in length and 145D in color, pollen; moderate in quantity and 12B in color.

*Fruit*.—Fruit and seed production has not been observed to date.

It is claimed:

1. A new and distinct variety of *Delosperma* plant named 'DE18-162' as described and illustrated herein.

* * * * *